US006476237B2

(12) United States Patent
Machac, Jr. et al.

(10) Patent No.: US 6,476,237 B2
(45) Date of Patent: Nov. 5, 2002

(54) PURIFICATION OF ALKYLENE CARBONATES

(75) Inventors: James R. Machac, Jr., The Woodlands, TX (US); Ralph M. DiGuilio, Round Rock, TX (US); John R. Sanderson, Austin, TX (US); Ronald L. Savage, Cedar Park, TX (US)

(73) Assignee: Huntsman Petrochemical Corporation, Austin, TX (US)

( * ) Notice: Subject to any disclaimer, the term of this patent is extended or adjusted under 35 U.S.C. 154(b) by 0 days.

(21) Appl. No.: 10/083,230

(22) Filed: Feb. 26, 2002

(65) Prior Publication Data

US 2002/0082430 A1 Jun. 27, 2002

Related U.S. Application Data

(63) Continuation-in-part of application No. 09/521,502, filed on Mar. 9, 2000, now Pat. No. 6,384,240.

(51) Int. Cl.[7] ............................................. C07D 317/36
(52) U.S. Cl. ...................................................... 549/230
(58) Field of Search .................................. 549/230, 228

(56) References Cited

U.S. PATENT DOCUMENTS

| 1,907,891 | A | 5/1933 | Steimmig et al. |
| 2,773,070 | A | 12/1956 | Lichtenwaler et al. |
| 4,233,221 | A | 11/1980 | Raines et al. |
| 4,314,945 | A | 2/1982 | McMullen et al. |
| 4,877,886 | A | 10/1989 | Ream |
| 4,952,542 | A | 8/1990 | Ream |
| 5,391,767 | A | 2/1995 | Mais et al. |
| 6,156,160 | A | 12/2000 | Marquis et al. ............... 203/29 |

FOREIGN PATENT DOCUMENTS

EP   0 540 225 B1   10/1992

*Primary Examiner*—T. A. Solola
*Assistant Examiner*—Kamal Saeed
(74) *Attorney, Agent, or Firm*—Russell R. Stolle; Ron D. Brown; Christopher J. Whewell

(57) ABSTRACT

Provided herein is a process for producing alkylene carbonates of ultra-high purity. According to the present invention, certain stages of traditional distillation of alkylene carbonate distillation are replaced by carbon treatment. Alkylene carbonates produced according to the invention have a color of less than 25 (Pt-Co), and are suitable for uses requiring ultra-pure alkylene carbonates.

11 Claims, 3 Drawing Sheets

PURIFICATION OF ALKYLENE CARBONATES

CROSS-REFERENCES TO RELATED APPLICATIONS

This Application is a continuation-in-part of U.S. Application Ser. No. 09/521,502 which was filed on Mar. 9, 2000 now U.S. Pat. No. 6,384,240, the entire contents of which are herein incorporated by reference thereto.

BACKGROUND OF THE INVENTION

This invention concerns a method for the purification of alkylene carbonates, especially high purity alkylene carbonates.

Alkylene carbonates are well known materials that have been produced commercially for decades. Alkylene carbonate may be manufactured by a variety of methods. One such method is described in U.S. Pat. No. 2,773,070 (1956). Some applications of alkylene carbonate demand use of very high purity products. For example, when alkylene carbonates are used as solvents for electrolyte salts in lithium batteries, the alkylene carbonate preferably contain essentially no impurities (e.g., glycol less than 20 parts per million ("ppm") and very low water amounts (also less than 20 ppm). In the past, such purification was accomplished, for instance, by treatment by distillation; however, the impure streams from the distillation tower(s), which may constitute up to 50 percent of the effluent from the carbonate reactor, are typically considered useless byproducts that are destroyed.

U.S. Pat. No. 6,156,160 ("the '160 patent"), the entire contents of which are herein incorporated by reference thereto, describes a process for the production and purification of alkylene carbonates. In one respect, the '160 patent teaches a process useful for the manufacture of alkylene carbonate, comprising: contacting carbon dioxide, an alkylene oxide, and a carbonation catalyst in a reaction zone to produce a crude reactor effluent; subjecting the crude reactor effluent to low temperature evaporation to form an evaporator overhead containing alkylene carbonate and an evaporator bottoms stream containing the catalyst, and recycling the evaporator bottoms stream to the reaction zone, removing any light components present in the evaporator overhead to form a second evaporator overhead and recycling the light components to the reaction zone; distilling the second evaporator overhead to form a first distillation overhead stream and a first distillation bottoms stream containing alkylene carbonate, and recycling the first distillation overhead stream to the reaction zone; distilling the first distillation bottoms stream to form a second distillation overhead stream and a second distillation bottoms stream and recycling the second distillation bottoms stream to the reaction zone; distilling the second distillation overhead stream to form a third distillation overhead stream and a third distillation bottoms stream and recycling the third distillation overhead stream to the reaction zone; distilling the third distillation bottoms stream to form a fourth distillation overhead stream containing purified alkylene carbonate and a fourth distillation bottoms stream, and recycling the fourth distillation bottoms stream to the reaction zone. In another respect, the '160 patent provides a process useful for the manufacture of an alkylene carbonate, comprising: distilling a first stream containing an alkylene carbonate in a purity of about 99 percent or more to form a first bottoms stream containing alkylene carbonate at a purity greater than the purification stream and an first overhead stream containing alkylene carbonate at a purity greater than the purification stream, and introducing the first overhead stream to an alkylene carbonate reactor; distilling the first bottoms stream to form a second overhead stream containing high purity alkylene carbonate and a second bottoms stream, and recycling the second bottoms stream to the alkylene carbonate reactor. In another respect, the '160 patent teaches a process useful for the manufacture of an alkylene carbonate, comprising: contacting carbon dioxide, an alkylene oxide, and a carbonation catalyst in a reactor to produce a crude reactor effluent; subjecting the crude reactor effluent to low temperature evaporation to form an evaporator overhead containing alkylene carbonate and an evaporator bottoms stream containing the catalyst, and recycling the evaporator bottoms stream to the reactor, removing any light components present in the evaporator overhead to form a second evaporator overhead and recycling the light components to the reactor; distilling the second evaporator overhead to form a first distillation overhead stream and a first distillation bottoms stream containing alkylene carbonate, and recycling the first distillation overhead stream to the reactor; distilling the first distillation bottoms stream to form a second distillation overhead stream and a second distillation bottoms stream and recycling the second distillation bottoms stream to the reactor; distilling the second distillation overhead stream in a distillation column to form a third distillation overhead stream, a high purity middle fraction having a purity of at least 99.99% and a third distillation bottoms stream, withdrawing the middle fraction from the column, and recycling the third distillation overhead stream and the third distillation bottoms stream to the reactor. In yet another respect, the '160 patent provides a process useful for the manufacture of ethylene carbonate, comprising: contacting carbon dioxide, an ethylene oxide, and a carbonation catalyst in a reactor to produce a crude reactor effluent; subjecting the crude reactor effluent to low temperature evaporation to form an evaporator overhead containing ethylene carbonate and an evaporator bottoms stream containing the catalyst, and recycling the evaporator bottoms stream to the reactor, removing any light components present in the evaporator overhead to form a second evaporator overhead and recycling the light components to the reactor; subjecting the second evaporator overhead to a second low temperature evaporation to form a less pure fraction and a more pure fraction, and recycling the less pure fraction to the reactor; and either: (1) distilling the more pure fraction in a distillation column to form a less pure overhead fraction, a high purity middle fraction having a purity of at least 99.99% and a less pure bottoms fraction, withdrawing the middle fraction from the column, and recycling the less pure overhead fraction and the less pure bottoms fraction to the reactor, or (2) distilling the more pure fraction to form a distillation overhead stream and a distillation bottoms stream and recycling the distillation overhead stream to the reactor; distilling the distillation bottoms stream to form a second distillation overhead stream containing purified alkylene carbonate having a purity of at least 99.99% and a second distillation bottoms stream, and recycling the second distillation bottoms stream to the reactor.

While it is believed to be representative of the current state of the art with respect to the manufacture and purification of alkylene carbonates, the '160 patent is not without its drawbacks, most notably the amount of overall energy consumed during alkylene carbonate production, and the final product yield. The present inventors have recognized that a need exists to further increase the efficiency of the alkylene carbonate production and purification process.

INVENTION SUMMARY

The present invention provides process for providing a purified alkylene carbonate from a crude alkylene carbonate, comprising the steps of: a) providing a crude alkylene carbonate by reacting carbon dioxide with an alkylene oxide in a reactor in the presence of a suitable catalyst; b) subjecting the crude alkylene carbonate to evaporation in a first evaporator to form a first evaporator overhead containing alkylene carbonate and a first evaporator bottoms stream containing the catalyst, and recycling the first evaporator bottoms stream to the reactor; c) subjecting the first evaporator overhead to evaporation in a second evaporator to form a second evaporator overhead containing light components present in the first evaporator overhead and recycling the light components to the reactor; and d) contacting the bottoms stream from the second evaporator with carbon to form a high purity alkylene carbonate product. Advantageously, the inventive process may be carried out using conventional equipment.

DETAILED DESCRIPTION

Alkylene Carbonate Production

Figure 1:
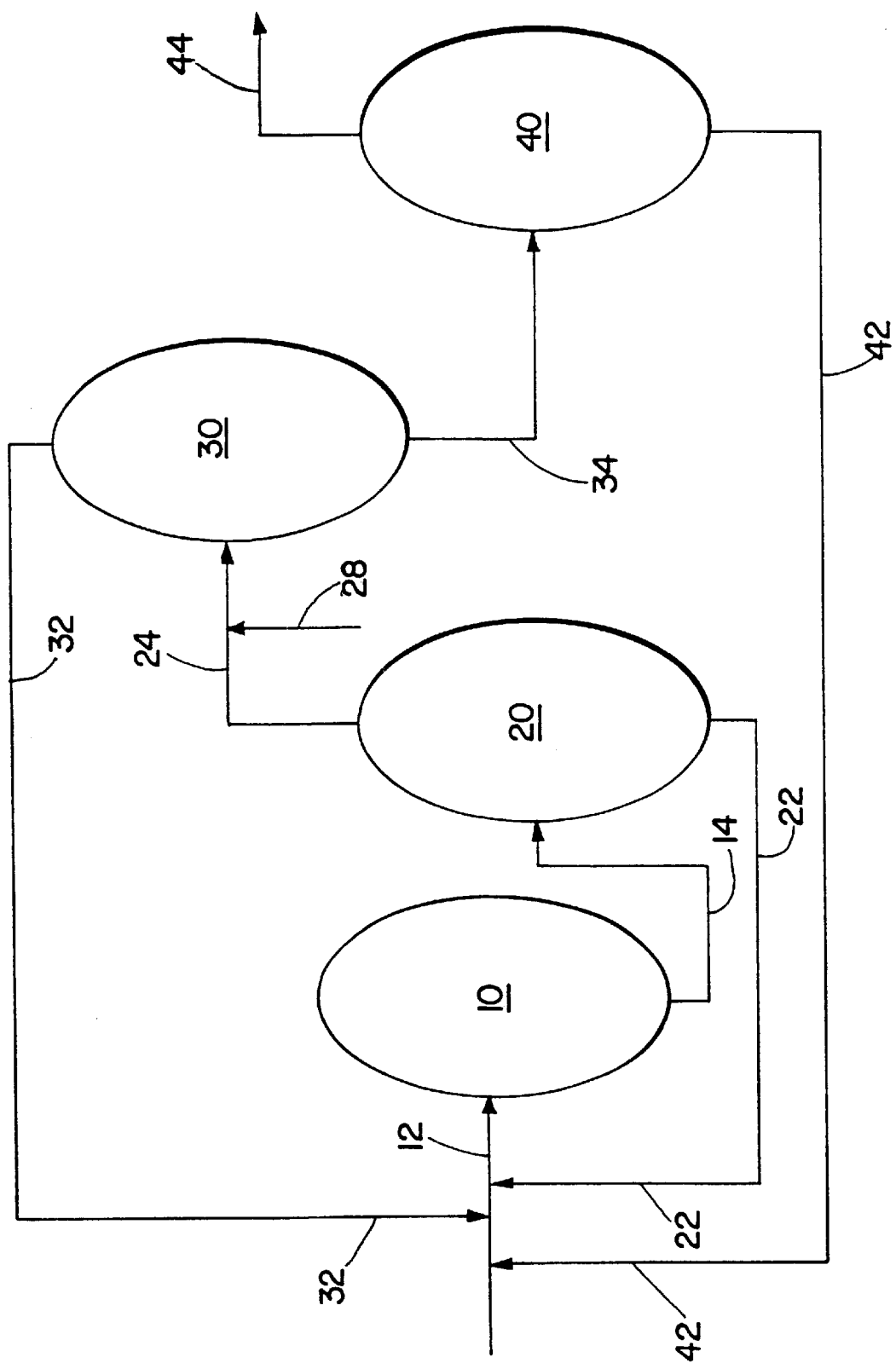
FIG. 1 shows a representative process scheme for the production and purification of alkylene carbonates according to one method.

In FIG. 1 there is shown a representative configuration for the practice of one process useful for producing and purifying alkylene carbonates. The starting reactants for production of alkylene carbonate, alkylene oxide and carbon dioxide, are introduced into the carbonate reactor 10 via line 12. While lines and conduits are depicted in FIG. 1, such lines and conduits need not necessarily be present, and the effluents may be conveyed between apparatuses and method.

In accordance with the prior art process of the '160 patent, alkylene oxides are reacted in reactor 10 with carbon dioxide in the presence of one or more catalysts comprising ammonium halides having the formula:

as is generally known in the art, wherein X is any halide ion, and $R_1$, $R_2$, $R_3$, and $R_4$ are each hydrogen, alkyl, aryl, alkenyl, alkaryl, or aralkyl in any combination or in which any two of the radicals $R_1$, $R_2$, $R_3$, and $R_4$ may be interconnected to form with the basic nitrogen atom a ring of the pyridine, piperidine, pyrollidine, pyrroline, morpholine, or thiomorpholine series. In certain embodiments, the alkyl group may contain from 1 to 20 carbon atoms, the aryl group may be phenyl or naphthyl, the alkenyl group may contain from 2 to 20 carbon atoms, the alkaryl group may be an alkyl substituted phenyl or naphthyl in which the alkyl group may contain from 1 to 4 carbon atoms and the aralkyl group may be an alkyl group that may contain from 1 to 4 carbon atoms substituted by a phenyl or naphthyl radical.

The alkylene oxides which may be employed as reactants in a process according to the invention are those of the oxirane system, which have a structural formula:

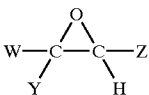

in which W, Y, and Z may be hydrogen, or alkyl groups containing from 1 to 20 carbon atoms, aryl groups containing from 6 to 12 carbon atoms, cycloalkyl groups containing from 5 to 20 carbon atoms, alkenyl containing from 2 to 20 carbon atoms, or in which any two of the groups W, Y, and Z may be interconnected to form with the two carbon atoms shown in the formula a carbocyclic ring. Ethylene oxide, propylene oxide, and butylene oxide are examples of such alkylene oxides.

The reaction is carried out at a temperature in the range of from about 100 degrees Centigrade to about 225 degrees Centigrade, preferably from about 175 degrees Centigrade to about 215 degrees Centigrade, and under a pressure of more than about 300 pounds per square inch gauge, preferably from about 1,000 to about 3,000 pounds per square inch gauge.

The reaction may be conducted either batchwise or continuously. For example, the catalyst may be continuously introduced in solution form along with the alkylene oxide and the carbon dioxide under desired pressure into one end of a reaction vessel and the products of reaction continuously withdrawn from the other end. A preferred solvent for the catalyst is the alkylene carbonate reaction product or a tertiary alcohol, e.g., tertiary butyl or amyl alcohol. Alternatively, batches of the alkylene oxide and the catalyst may be introduced into an autoclave or bomb type of reactor, the desired pressure built up by introducing carbon dioxide and the reaction mixture agitated while being heated to the reaction temperature and maintained under a superatomospheric pressure of carbon dioxide. Irrespective of whether a batch or continuous procedure is followed, each unit weight of reactants and reaction products resulting therefrom is maintained at reaction temperature and pressure for from about 1 to about 90 minutes, preferably from about 30 to about 60 minutes. This time interval is referred to herein as the reaction time.

The alkylene oxide and carbon dioxide are mixed in proportions to provide an excess of carbon dioxide over and above the stoichiometric amount required for reaction. This excess may be of the order of from 1% to 500% by weight. The ammonium halide may be obtained as such from any available source or produced in any desired manner. While ammonium iodides, bromides, chlorides, and fluorides are all of them effective in catalyzing the synthesis of alkylene carbonates from alkylene oxides and $Co_2$, the iodides and bromides are generally considered to be more effective than the chlorides and fluorides. It is preferred to use the bromides since they are highly effective and in addition are much more stable under conditions of use than are the iodides, which tend to decompose on heating with evolution of elemental iodine which poses an additional purification problem. The ammonium radical may be unsubstituted $(NH_4)^+$ or mono-, di-, tri-, or tetrasubstituted. Preferably, a tetrasubstituted ammonium halide is employed.

Representative examples of preferred catalysts include but are not limited to tetraethyl ammonium bromide, tetramethyl ammonium bromide, benzyltriethyl ammonium bromide and tetrabutyl ammonium bromide. These catalysts may easily be produced by heating a tertiary amine with an alkyl bromide. Thus, from triethyl amine and benzyl bromide, benzyltriethyl ammonium bromide is obtained.

The ammonium halide catalysts may be purified by crystallization from a suitable solvent: in most cases an alcohol may be used for this purification. Methyl and ethyl alcohols are satisfactory for this purification in the case of most ammonium halides; however, a preferred solvent for tetraethylammonium bromide is tertiary butyl alcohol in which the catalyst is almost completely insoluble at room temperature, but in which it is quite soluble near the boiling point. Tertiary amyl alcohol is similarly well suited for this use.

The amount of catalyst used in general should be from 0.1% to 10%, preferably from about 1 to about 5% based on the weight of the reaction mixture. In general, the greater the catalyst concentration, within these limits, the more rapid and complete the reaction.

The carbonate reactor may be operated as described in U.S. Pat. No. 2,773,070 and W. J. Peppel, "Preparation and Properties of the Alkylene Carbonates," Industrial and Engineering Chemistry, Volume 50, Number 5, May, 1958. The reactor 10 may be of conventional design as is currently being used in industry for this reaction.

The crude reactor effluent from reaction 10 may be conveyed via line 14 to an evaporation apparatus 20. The evaporation apparatus 20 may be of conventional design and is operated such that a low residence time is maintained to minimize degradation of the catalyst at high temperatures. The bottoms from the evaporator 20 contain inter alia, the catalyst. The overhead contains alkylene product and lights. The evaporator may be, for example, a wiped film evaporator or falling film tower. Typically, the evaporator is operated at a temperature from about 50 to about 150 degrees Centigrade, and at a pressure of from about 0.1 to about 100 mm Hg. If the catalyst is not sensitive to high temperatures, it may not be necessary to employ an evaporator having low residence time. The bottoms may be recycled to the reactor 10 via conduit 22. Typically, the evaporator splits the material such that about 5 to about 20 percent exit as bottoms, with about 80 to about 95 percent being overhead. The alkylene carbonate product stream exiting the evaporator usually has a purity in the range of about 98 to about 99.5. Optionally, a second evaporator may be employed in series, again with the less pure fractions being returned to the reactor.

Optionally, the effluent from reactor 10 may be sent to a finishing drum, not shown. After removing lights from the evaporator overhead (using for instance a low pressure separator and/or a gas-liquid separator), the overhead is sent, directly or indirectly, to a first distillation tower 30 via line 24. The product may for example be sent to a storage unit prior to distillation. The first distillation tower, and all distillation towers used herein, serve to further purify the alkylene carbonate. The first distillation tower may be operated at any temperature and pressure which will afford a first distillation bottoms that is a higher purity than the alkylene carbonate received from the evaporator. In general, the first distillation tower is operated at a temperature of from about 50 degrees Centigrade to about 150 degrees Centigrade and a pressure of from about 0.1 to about 100 mm Hg.

The overhead from the first distillation tower may be recycled to reactor 10 via line 32. The first distillation bottoms, which constitutes about 90 to about 99 percent of the material fed to the first distillation tower, exits the first tower 30 via conduit 34, and is transferred to the second distillation tower 40.

In second distillation tower 40, the first distillation bottoms is subjected to additional purification. The second distillation bottoms may be recycled to the reactor 10 via conduit 42. The purified alkylene carbonate exits the second tower 40 via line 44. The purity of the alkylene carbonate stream exiting the second distillation column is usually in the range from about 99.5 to about 99.95 percent.

To achieve even further purification, the second distillation overhead is then subjected to two additional distillations. The additional distillations may be accomplished in a variety of ways. For example, the second distillation overhead may be stored and reintroduced into first distillation tower 30 via line 28. This would be done when the reactor 10 and evaporator 20 were not running. The overhead from the first distillation tower 30 and bottoms from the second distillation tower 40 would again be recycled to reactor 10. This recycling provides many advantages. The most important advantages are conservation of mass, which provides a high overall yield, and a cost advantage as contrasted against processes where such overhead and bottoms destroyed or not used to make additional high purity alkylene carbonate.

In another alternative, the second distillation overhead is sent to another tower or towers different from the towers 30 and 40 shown in FIG. 1. For example, the overhead may be sent to a single, very large tower instead of two smaller towers in series. The larger tower may have 50 to 150 theoretical plates containing for instance 100 trays and packing, as opposed to smaller towers having 40 to 60 trays. In this case, the middle fraction from the large tower is the high purity alkylene carbonate, with the overhead and bottoms being recycled to the reactor 10. Hence, recycling of fractions to the reactor 10 would still be performed even if a single tower were used or if the effluent was sent to other towers, off-site or otherwise, for further purification. It should be appreciated that an important aspect of a particular process for producing alkylene carbonates is the return of the less pure fractions to the reactor, which leads to higher yields, less waste and a more economical high purity alkylene carbonate process.

Figure 2:
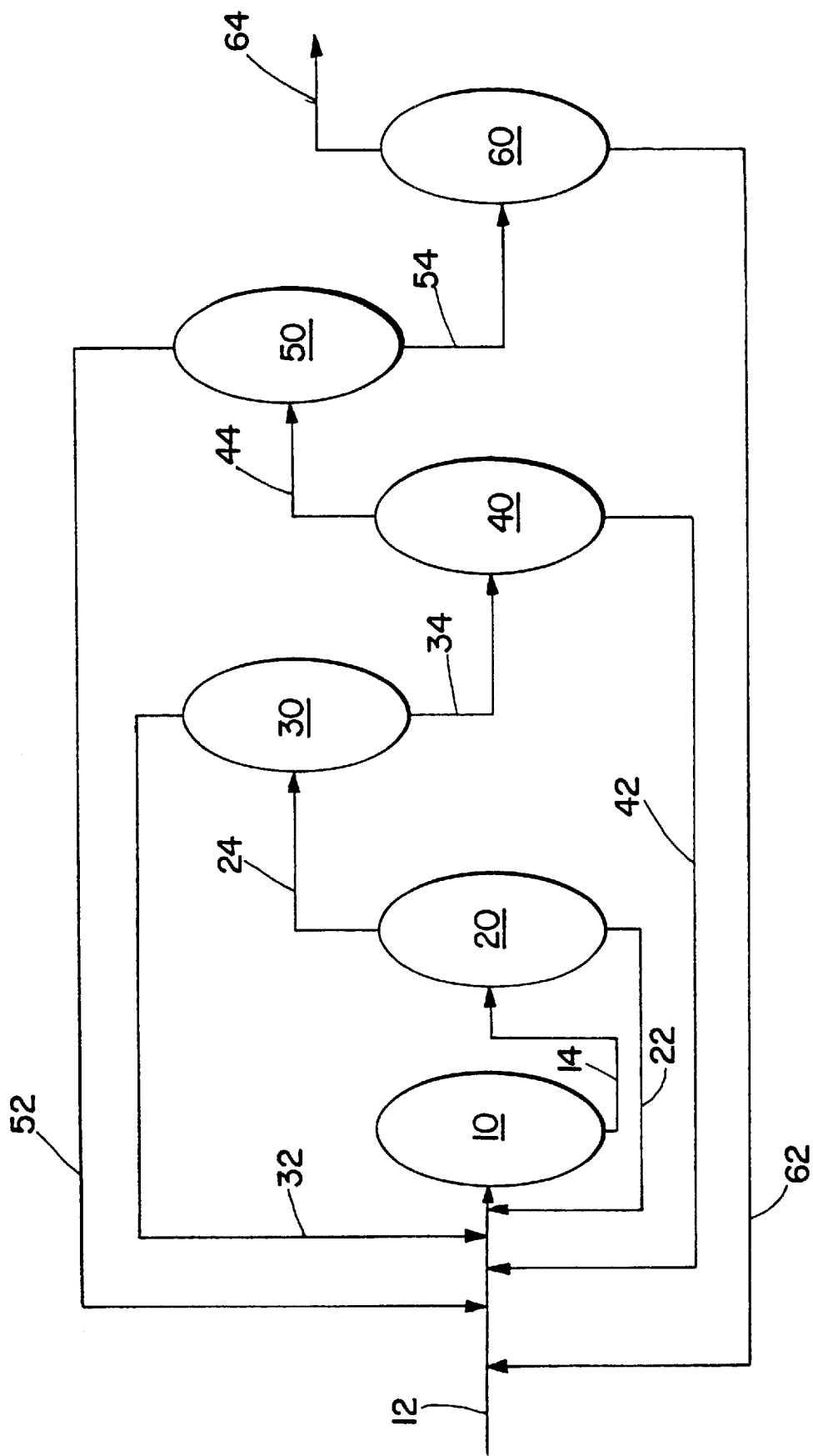
FIG. 2 shows another representative process scheme for the production and purification of alkylene carbonates according to an alternative method.

Still another alternative is depicted in FIG. 2. In this generalized scheme, four towers are used in series. FIG. 2 is identical to FIG. 1 except additional columns 50 and 60 are included. Instead of sending product effluent from second distillation tower 40 to first distillation tower 30 or to a separate distillation tower or towers, the effluent flows into the third distillation tower 50 via line 44. The overhead from the third distillation tower 50 is recycled to reactor 10. The third distillation bottoms is introduced into fourth distillation tower 60 via line 54. The fourth distillation bottoms is recycled to line 12 and reactor 10 via conduit 62. The final alkylene carbonate product exits the fourth distillation tower via line 64.

In general, the distillation towers (also referred to as columns) may be of conventional design. The towers may be packed with conventional packing. The temperature and pressure in the tower may be adjusted depending on the type of alkylene carbonate being produced. In general, particularly for ethylene carbonate and propylene carbonate, the tower is maintained at a temperature in the range from about 50 degrees Centigrade to about 150 degrees Centigrade, and the pressure is in the range from about 0.1 to about 100 mm Hg.

The final alkylene product produced by the process of a prior art process has a purity of at least 99.99 percent. Typically the final alkylene carbonate has a purity up to 100 percent and more typically more than about 99.999 percent. The final product typically has a water content less than about 20 parts per million ("ppm") and impurity levels less than 20 ppm.

It should also be appreciated that the alkylene carbonate may be made in the reactor from a variety of methods, such as from ethylene glycol and phosgene such as described in Neminowsky, J. prakt. Chem., [2] 28, 3789 (1955); from diethyl carbonate and ethylene glycol by transesterification as described in Morgan et al., J. Am. Chem. Soc., 75, 1263 (1053); from ethylene chlorohydrin and sodium bicarbonate as described in U.S. Pat. No. 1,907,891; or from 1,2-epoxides and carbon dioxide as described in German patent 740,366 (1943).

The process of producing alkylene carbonates in the above-described ways, including each sub-step of the overall process, may be operated continuously, intermittently, or as a batch process.

Alkylene Carbonate Production According to The Inventive Process

The same principles described above and in the '160 patent as being useful for the formation of an alkylene carbonate are also useful in preparing an alkylene carbonate according to the present invention. However, according to the present invention, the alkylene carbonate produced in the reaction is purified by a single pass distillation in which the glycol and water present in the product stream is taken overhead, and the bottoms in the column are treated with carbon to remove color, excess water, and excess glycol. The fact that the present invention can be carried out effectively is surprising, since the teachings of the prior art indicate that carbon treatment of alkylene carbonates with carbon results in decomposition of the alkylene carbonate.

A process according to the invention produces high purity alkylene carbonate and has reduced yield losses over prior art methods, such as those disclosed in the '160 patent. Additionally, the distillation conditions are less aggressive since the final product "polish" is via the carbon. Owing to its relative simplicity, less capital equipment is needed to carry out a process according to the invention.

Figure 3:
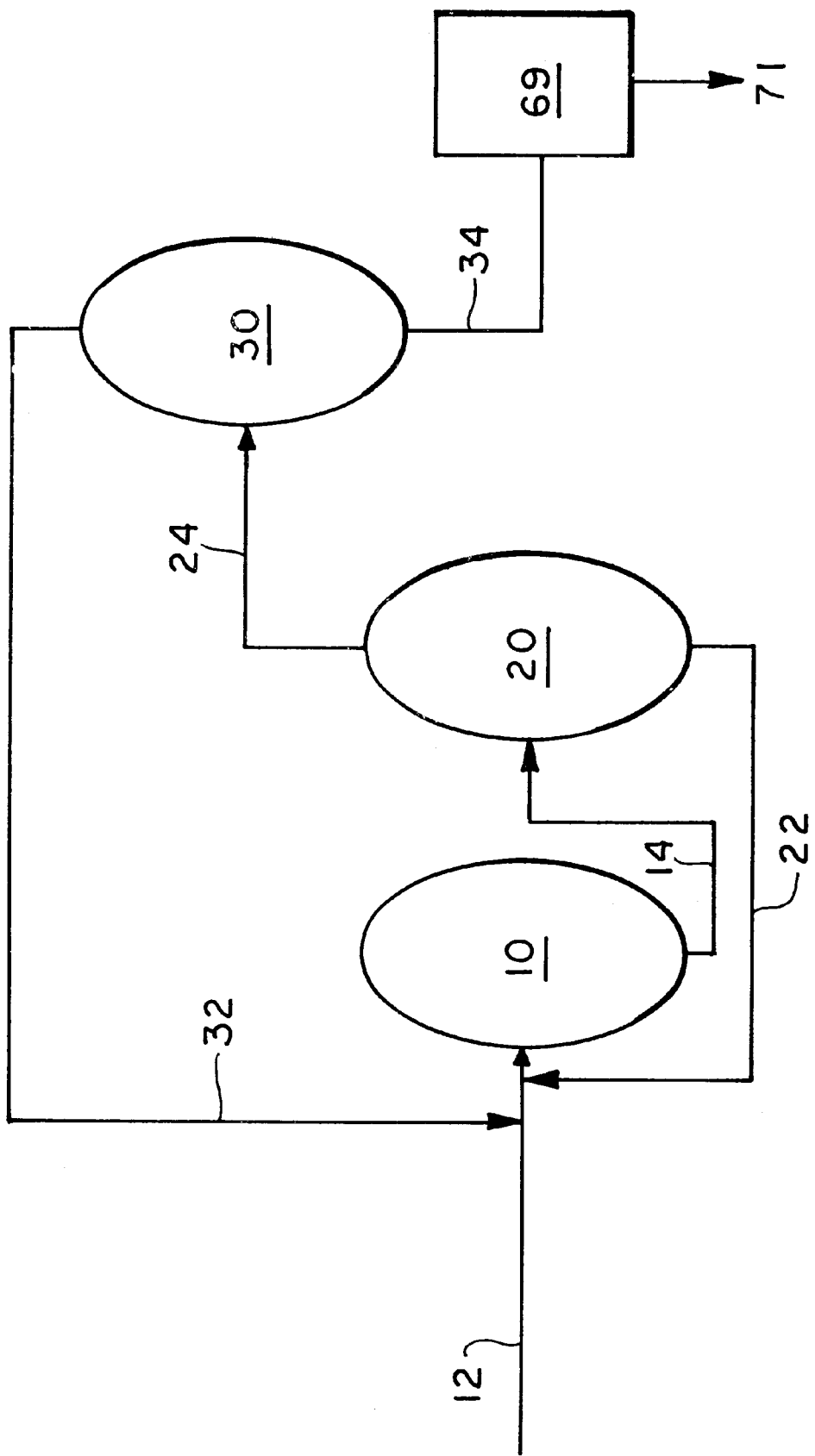
FIG. 3 shows a representative process scheme for the production and purification of alkylene carbonates according to the present invention.

Referring to FIG. 3, there is shown a process scheme according to one form of the present invention. In this figure, the starting reactants for alkylene carbonate production are fed through line 12 to reactor 10, in which a suitable catalyst, as previously described herein, resides. The crude effluent from reactor 10 is conveyed via line 14 to an evaporation apparatus 20, which again is of conventional design and is operated such that a low residence time is maintained to minimize degradation of the catalyst at high temperatures. The bottoms from the evaporator 20 contain quantities of the catalyst, and the overhead contains alkylene carbonate product and lights. The bottoms are preferably recycled to the reactor via line 22, and the overhead is preferably sent to the first distillation tower 30 via line 24. The overhead from the first distillation tower 30 may be recycled to reactor 10 via line 32. The first distillation bottoms product exits the first distillation tower 30 via conduit 34 and is directed to carbon treatment bed 69. Following carbon treatment, the product 71 is of ultra high purity.

Carbon treatment is a process in which a liquid substance is brought into contact with solid elemental carbon. Carbons useful for treatment of liquid streams for various purposes are known in the art. Typically such carbons used are known as "activated carbon", and typically activated carbons exist in a particulate form. Activated carbon may comprise acid-washed activated carbon. Activated carbon typically has an internal surface area of from about 500 $g/m^2$ to about 1500 $g/m^2$. One carbon useful in a process according to the present invention is the carbon known as "GLY-400" available from Calgon Carbon Corporation of Houston, Texas. Another carbon useful in a process according to the present invention is the carbon known as "B&S Carbon" available from Barneby and Sutcliffe of Columbus, Ohio. Another carbon useful in a process according to the present invention is the carbon known as NORIT® RD 0.8 available from Norit Corporation of the Netherlands. The most preferred carbon useful in a process according to the present invention is the carbon known as "GLY-400" available from Calgon Carbon Corporation of Houston, Tex.

In the context of the present invention, the liquid substance to be treated is the bottoms from the distillation tower 30. According to a preferred form of the invention, the bottoms stream from the distillation tower 30 (comprising mostly alkylene carbonate) is contacted with activated carbon for an effective time period to cause sufficient adsorption of impurities present in the alkylene carbonate to yield an alkylene carbonate having 99.99 percent purity. To achieve such a level of purity, it is generally desirable that the percentage of alkylene carbonate product in the bottoms stream 34 be at least 99.9% alkylene carbonate, and that the bottoms stream experience a space velocity of at least 0.1 to 2.0. The impurities typically comprise water, glycols, and color bodies. By a process of the present invention, it is possible to produce essentially colorless alkylene carbonates, i.e., those having a color of less than 25 on the platinum-cobalt scale commonly in use to measure color.

Although one embodiment of the present invention treats the bottoms stream of the distillation tower 30 in a process described by the overall reaction scheme represented in FIG. 3, the present invention is also suitable for treating crude mixtures of alkylene carbonates produced using reaction schemes other than those embodied in FIG. 3, including, without limitation, those described in U.S. Pat. Nos. 4,314,945; 4,325,874; 5,349,077; and 6,258,962 with the only requisite being that the process stream being treated is one which comprises at least 99.9% by weight of alkylene carbonate. A stream of an alkylene carbonate which results from a chemical reaction that is carried out for the purpose of producing an alkylene carbonate, which stream contains at least 99.9% of alkylene carbonate, along with impurities comprising water, glycols, color bodies, and/or other impurities attendant to the process carried out, may be referred to as a crude alkylene carbonate for purposes of this specification and the appended claims.

Further modifications and alternative embodiments of the inventive process will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as illustrative embodiments. Equivalent elements or materials may be substituted for those illustrated and described herein, and certain features of the invention may be utilized independently of the use of other features, all as would be apparent to one skilled in the art after having the benefit of this description of the invention.

What is claimed is:

1. A process for providing a purified alkylene carbonate from a crude alkylene carbonate comprising the steps of:
    a) providing a crude alkylene carbonate by reacting carbon dioxide with an alkylene oxide in a reactor in the presence of a suitable catalyst;
    b) subjecting the crude alkylene carbonate to evaporation in a first evaporator to form a first evaporator overhead containing alkylene carbonate and a first evaporator bottoms stream containing the catalyst, and recycling the first evaporator bottoms stream to the reactor;

c) subjecting the first evaporator overhead to evaporation in a second evaporator to form a second evaporator overhead containing light components present in the first evaporator overhead and recycling the light components to the reactor; and d) contacting the bottoms stream from the second evaporator with carbon to form a high purity alkylene carbonate product.

2. A process according to claim 1 wherein said alkylene carbonate is selected from the group consisting of: ethylene carbonate, propylene carbonate, and butylene carbonate.

3. A process according to claim 1 wherein said first evaporator and said second evaporator of the type selected from the group consisting of: a wiped film evaporator and a falling film tower.

4. A process according to claim 1 wherein both evaporations conducted in said first evaporator and said second evaporator are conducted under a temperature in the range of 50 degrees Centigrade to 150 degrees Centigrade.

5. A process according to claim 1 wherein both evaporations conducted in said first evaporator and said second evaporator are conducted under a pressure in the range of 0.1 mm Hg to 100 mm Hg.

6. A process according to claim 1 wherein the catalyst is a tetraalkyl ammonium halide.

7. A process according to claim 1 wherein the catalyst is a tetraethyl ammonium bromide.

8. A process according to claim 1 wherein the reacting carbon dioxide with an alkylene oxide in a reactor is conducted at a temperature in the range of 170 degrees Centigrade to about 190 degrees Centigrade.

9. A process according to claim 1 wherein the bottoms stream from the second evaporator is contacted with carbon at a temperature in the range of 10 degrees Centigrade to 50 degrees Centigrade.

10. A process according to claim 1 wherein the bottoms stream from the second evaporator is contacted with carbon in a continuous manner and at a flow rate in the range of from 1 milliliter to 50 milliliters of alkylene carbonate per milliliter of carbon per hour.

11. A process according to claim 1 wherein said carbon has been pre-treated with an inorganic acid.

* * * * *